(12) United States Patent
Wang et al.

(10) Patent No.: US 9,499,556 B2
(45) Date of Patent: Nov. 22, 2016

(54) CONVENIENT PREPARATION OF N-SUBSTITUTED MORPHINAN-6-OLS FROM MORPHINAN-6-ONES

(71) Applicant: MALLINCKRODT LLC, Hazelwood, MO (US)

(72) Inventors: Peter X. Wang, Creve Coeur, MO (US); Tao Jiang, Chesterfield, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 14/529,368

(22) Filed: Oct. 31, 2014

(65) Prior Publication Data

US 2015/0126741 A1    May 7, 2015

Related U.S. Application Data

(60) Provisional application No. 61/898,634, filed on Nov. 1, 2013.

(51) Int. Cl.
*C07D 489/08*    (2006.01)

(52) U.S. Cl.
CPC .................................. *C07D 489/08* (2013.01)

(58) Field of Classification Search
CPC .................................................... C07D 487/08
See application file for complete search history.

(56) References Cited

U.S. PATENT DOCUMENTS

| | | | |
|---|---|---|---|
| 7,465,797 B2 | 12/2008 | Ghoshal | |
| 2007/0191595 A1 | 8/2007 | Ghoshal | |

FOREIGN PATENT DOCUMENTS

| | | | |
|---|---|---|---|
| WO | 2006/035195 A1 | 4/2006 | |
| WO | 2007/137785 A2 | 12/2007 | |
| WO | 2007137785 | * 12/2007 | |
| WO | 2008/137672 A1 | 11/2008 | |
| WO | 2010/132570 A1 | 11/2010 | |
| WO | 2011/021029 A1 | 2/2011 | |
| WO | 2013/003720 A1 | 1/2013 | |
| WO | 2015066443 A1 | 5/2015 | |

OTHER PUBLICATIONS

International Search Report and Written Opinion for related International application No. PCT/US2014/063372 dated Feb. 24, 2015, 9 pgs.

* cited by examiner

*Primary Examiner* — Rita Desai

(57) ABSTRACT

Described herein are methods of preparing 6-hydroxy N-alkyl morphinan-6-ols from morphinan-6-ones, as illustrated below:

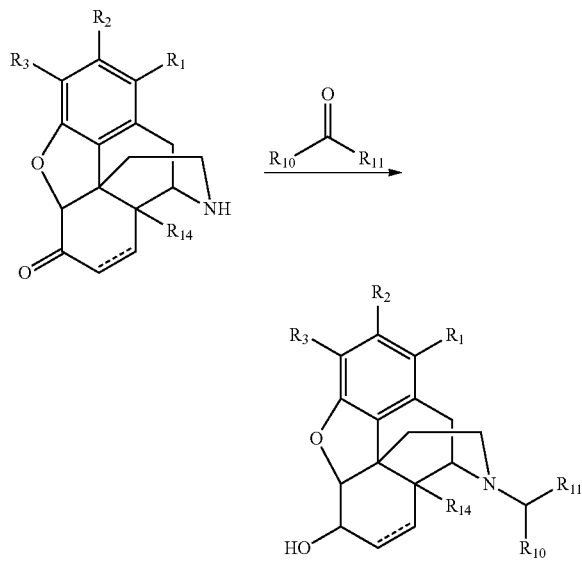

wherein the variables $R_1$, $R_2$, $R_3$, $R_{10}$, $R_{11}$, $R_{14}$, and === are as defined herein and wherein the reactions occur in a one-pot procedure using a boron based reducing agent.

18 Claims, No Drawings

CONVENIENT PREPARATION OF N-SUBSTITUTED MORPHINAN-6-OLS FROM MORPHINAN-6-ONES

CROSS-REFERENCE TO RELATED APPLICATIONS

This application claims the priority of U.S. provisional application Ser. No. 61/898,634, filed Nov. 1, 2013, which is hereby incorporated by reference in its entirety.

FIELD OF THE INVENTION

Disclosed herein are methods of preparing N-alkyl morphinan-6-ols from morphinan-6-ones, in a one-pot procedure.

BACKGROUND OF THE INVENTION

N-substituted morphinan-6-ols such as naltrexol, naloxol, and nalbuphine, are important narcotic pharmaceuticals. The current processes for preparing such compounds either 1) comprise several separate steps in which the introduction of the nitrogen substituent is performed before or after the reduction of the 6-keto group to an alcohol, or 2) conduct a one-pot procedure but use a transition metal catalyst and hydrogen gas. The first route is inefficient, while the second route is susceptible to catalyst poisoning, does not afford acceptable stereoselectivity, and/or requires the use of expensive, chiral catalysts. Therefore, there is a need for a cost effective, one-pot process that affords high diastereomeric purity.

SUMMARY OF THE INVENTION

Disclosed herein are methods of preparing compounds of formula (I),

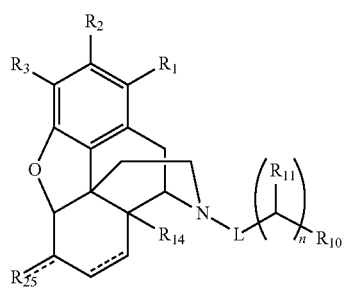

(I)

the methods comprising, contacting compounds of formula (II)

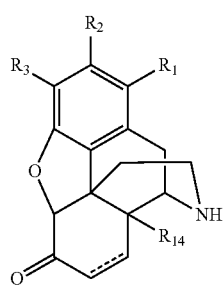

(II)

with a boron based reducing agent, and a carbonyl compound of the formula:

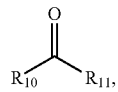

an acylating agent, or
an alkylating agent, wherein
the contacting is optionally conducted in a solvent; and wherein
at each occurrence, === is independently a single or double bond;
L is absent, —C(O)— or —SO$_2$—;
n is 0 or 1;
$R_1$ is H, $C_1$-$C_6$ alkyl, $C_1$-$C_6$ alkoxy, OH, or —O-Pro;
$R_2$ is H, $C_1$-$C_6$ alkyl, $C_1$-$C_6$ alkoxy, OH, or —O-Pro;
$R_3$ is H, $C_1$-$C_6$ alkyl, $C_1$-$C_6$ alkoxy, OH, or —O-Pro, wherein
Pro, at each occurrence, is independently a hydroxyl protecting group;
$R_{10}$ is $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl;
$R_{11}$ is H, absent, $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl;
wherein each aryl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy; and
wherein each heteroaryl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy; and
wherein each heterocycloalkyl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy;
$R_{14}$ is H or OH; and
$R_{25}$ is O if === is a double bond, or $R_{25}$ is OH, if === is a single bond;
provided that when the compound of formula (II) is contacted with the carbonyl compound, n is 1 and L is absent;
provided that when the compound of formula (II) is contacted with the acylating agent, L is —C(O)— or —SO$_2$—; and when the acylating agent is an acid anhydride, then n is 0; and
provided that when the compound of formula (II) is contacted with the alkylating agent, L is absent.

Also disclosed herein are one-pot methods wherein the NH group of formula (II) is treated with a carbonyl compound, such as an aldehyde or ketone, and a reducing agent (preferably a boron based reducing agent), and wherein the 6-keto group is reduced to a 6-hydroxy group.

Furthermore, disclosed herein are one-pot methods wherein the NH group of formula (II) is contacted treated with an alkylating agent and a base, thereby generating an N-alkyl group, and wherein the 6-keto group is reduced to a 6-hydroxy group by the addition of a reducing agent. Alternatively, the reduction of the 6-keto group to the 6-hydroxy group may be conducted before NH group is alkylated.

One-pot methods wherein the NH group of formula (II) is acylated with an acylating agent and a base, thereby generating an N-acyl group, and wherein the 6-keto group is reduced to a 6-hydroxy group by the addition of a reducing agent are also disclosed herein. Alternatively, the reduction of the 6-keto group to the 6-hydroxy group may be conducted before NH group is alkylated.

DETAILED DESCRIPTION

In general, the morphinans detailed herein include any compound comprising a morphinan structure as diagrammed below. For the purposes of illustration, the ring atoms of the core morphinan structure are numbered as diagrammed below, wherein R is hydrogen, hydrocarbyl or substituted hydrocarbyl:

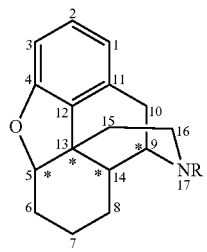

Morphinan compounds have asymmetric centers. In particular, the core morphinan compound may have at least four chiral carbons (designated by asterisks); namely, C-5, C-13, C-14, and C-9. Thus, each chiral center may have an R or an S configuration. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or are both on the beta face of the molecule. Thus, the compounds disclosed herein may have a (−) or a (+) orientation with respect to the rotation of polarized light.

For the sake of clarity, it should be noted that when n is 0, the compound of formula (I) becomes:

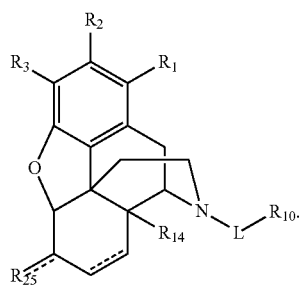

As described above, disclosed herein are methods of converting compounds of formula (II) into compounds of formula (I) via a one-pot process. In the disclosed one-pot processes, preferably, two transformations occur. One is the reduction of the 6-keto group to the 6-hydroxy group, and the other is replacing the hydrogen on the NH group with one of the groups described herein.

When the 6-keto group of formula (II) is reduced, a mixture of 6-alpha-hydroxyl and 6-beta-hydroxy epimers are formed. Without wishing to be bound to a particular theory, it is believe that the steric size of the reducing agent favors the formation of the 6-alpha-hydroxy epimer. The epimeric ratio of the 6-alpha-hydroxy morphinan epimer to the 6-beta-hydroxy morphinan epimers is generally greater than or equal to 9:1. More preferably, the epimeric ratio may be greater than or equal to 95:5. Still more preferably, the epimeric ratio may be greater than or equal to 96:4. More preferably still, the ratio may be greater than or equal to 97:3. Still more preferably, the epimeric ratio may be greater than or equal to 98:2. Most preferably, the epimeric ratio may be greater than or equal to 99:1.

If desired, the methods disclosed herein may be conducted in a solvent or a mixture of solvents. In general, the solvent may be an aprotic polar solvent. Non-limiting examples of suitable aprotic solvents include acetonitrile, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. In certain embodiments, the solvent may be tetrahydrofuran (THF), dichloromethane, dimethylformamide (DMF), dimethylacetamide (DMA), N-methylpyrrolidine (NMP) or combinations thereof. In exemplary embodiments, the methods may be conducted in DMF, DMA, NMP, or combinations thereof.

In general, the weight to weight ratio of the solvent to the compound of formula (II) may range from about 0.5:1 to about 100:1. In various embodiments, the weight ratio of the solvent to the compound of formula (II) may range from 0.5:1 to about 5:1, from about 5:1 to about 25:1, or from about 25:1 to about 100:1. In exemplary embodiments, the weight ratio of the solvent to the compound of formula (I) may range from about 0.5:1 to about 10:1.

The methods disclosed herein utilize large, sterically hindered reducing agents. Preferably, the reducing agent is a hydride reducing agent. Still more preferably, it is a boron based reducing agent. One preferred boron reducing agent may be $MBH_nR_{4-n}$, wherein M is Li, Na, or K; n is 1 or 2; and each R is independently $—O_2C—(C_1-C_5$ alkyl), with M being Na or K more preferred than Li, and Na being preferred over K. Additionally, in a preferred aspect, the "$—O_2C—(C_1-C_5$ alkyl)" group may be "$—O_2CCH_3$." A preferred reducing agent, that is capable of reducing the 6-keto to a hydroxyl and the imine formed when the NH group reacts with an aldehyde or ketone, may be sodium triacetoxyborohydride, which has the following formula: $NaBH(O_2CCH_3)_3$.

When the sterically hindered, boron reducing agent is added to the reaction mixture, it may be added as a solid, or it may be dissolved in a solvent or combination of solvents. Preferably, it is dissolved in a solvent or mixture of solvents that are the same as those used in the reaction mixture.

The amount of reducing agent used can and will vary depending upon the number of transformations the reducing agent conducts. In general, from about 1 to about 10 equivalents of the reducing agent may be used. It is preferred to use the least amount of reducing agent necessary to conduct the desired transformation(s). In certain embodiments, the amount of reducing agent may range from about 1 to about 2 equivalents, from about 2 to about 4 equivalents, or from about 4 to about 10 equivalents. In exemplary embodiments, from about 2 to about 3.5 equivalents of the reducing agent may be used.

The reaction temperatures and times may vary, depending on the nature of the transformation or transformations that are being conducted. Typically, the reactions are conducted at temperatures from about 0° C. up to the reflux temperature of the solvent. In some embodiments, the temperature of the may range from about 0° C. to about 100° C. In other embodiments, the temperature of the may range from about 0° C. to about 30° C., or more preferably at about 20° C. Reaction times typically range from about 10 minutes up to about 48 hours. For example, the reaction time may range from about 3 hours to about 8 hours, or from about 8 hours to about 20 hours. The ability to determine more specific temperatures and times is within the abilities of one having ordinary skill in the art.

When conducting the methods described herein, various orders of mixing the reagents may be used, and the order may depend on the specific transformation(s) that occur.

In one aspect, the compounds of formula (II) are contacted with a reducing agent (as described above) and an aldehyde or ketone of the formula

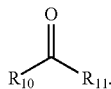

More preferably, $R_{10}$ is $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl; and $R_{11}$ is H, $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl;

wherein each aryl group is independently phenyl or naphthyl, and each aryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy;

wherein each heteroaryl group is independently pyrrolyl, imidazolyl, triazolyl, pyridyl, pyridazinyl, pyrimidyl, pyrazinyl, triazinyl, indolyl, quinolinyl, furanyl, benzofuranyl, thienyl, or benzothienyl, and each heteroaryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy; and wherein each heterocycloalkyl group is pyrrolidinyl, imidazolidinyl, oxazolidinyl, thiazolidinyl, tetrahydrofuranyl, piperidinyl, piperazinyl, or morpholinyl, and each heterocycloalkyl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy.

Still more preferably, $R_{10}$ is $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl; and $R_{11}$ is H, $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl;

wherein each phenyl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_4$ alkoxy, OPro, halo, $C_1$-$C_4$ haloalkyl or $C_1$-$C_4$ haloalkoxy.

In one preferred embodiment, $R_{11}$ is H.

In one preferred embodiment, $R_1$ is H and $R_2$ is H and $R_3$ is OH, methoxy or OPro, wherein Pro is as defined herein.

In one embodiment, $R_{25}$ is OH and $\equiv$ is a single bond.

In an alternate embodiment, $R_{25}$ is O and $\equiv\equiv\equiv$ is a double bond.

When conducting the reductive amination reaction, typically from about 1 to about 10 equivalents of aldehyde or ketone may be used. In various embodiments, the amount of aldehyde or ketone used may range from about 1 to about 2 equivalents, from about 2 to about 4 equivalents, or from about 4 to about 10 equivalents. In one embodiment, about 1.0 to about 1.2 equivalents of aldehyde or ketone may be used.

If desired, an acid may be added to the reaction mixture. Acceptable acids include the mineral acids, such as HCl or $H_2SO_4$, or organic acids, such as formic acid or acetic acid. If desired, a combination of two or more acids may be used. A preferred acid is acetic acid.

In various embodiments, the compound of formula (II) may be noroxycodone, norhydromorphone, norhydrocodone, normorphinone, or norcodeinone. In one embodiment, the compound of formula (II) may be noroxymorphone, which has the following structure:

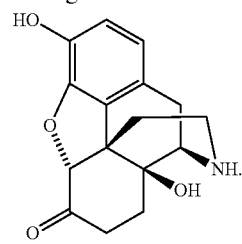

In this iteration, compounds of formula (I) that can be made using the methods described herein include, but are not limited to nalbuphine, 6α-naltrexol, nalbuphone, and naltrexone, which have the following structures:

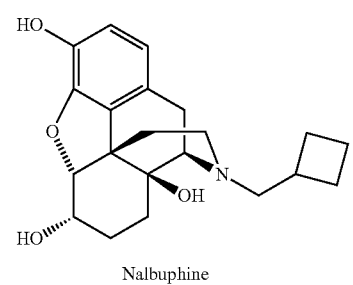

Nalbuphine

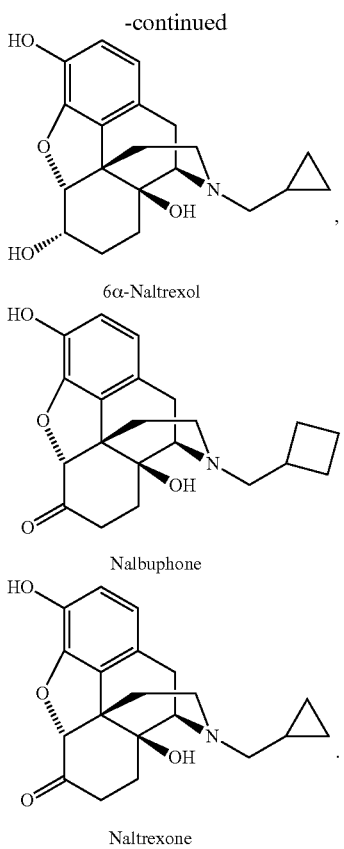

6α-Naltrexol

Nalbuphone

Naltrexone

In an embodiment, the compound of formula (II) is noroxymorphone, and the compound of formula (I) is nalbuphine.

In another embodiment, the compound of formula (II) is noroxymorphone and the compound of formula (I) is 6α-naltrexol.

In yet another embodiment, the compound of formula (II) is noroxymorphone and the compound of formula (I) is naltrexone.

In still another embodiment, the compound of formula (II) is noroxymorphone and the compound of formula (I) is nalbuphone.

In an alternative aspect, the compounds of formula (II) are contacted with a reducing agent (as described above) and an alkylating agent. Examples of alkylating agents include those of the formula

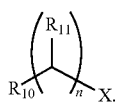

More preferably, $R_{10}$ is $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl; and $R_{11}$ is H, $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl;

wherein each aryl group is independently phenyl or naphthyl, and each aryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy;

wherein each heteroaryl group is independently pyrrolyl, imidazolyl, triazolyl, pyridyl, pyridazinyl, pyrimidyl, pyrazinyl, triazinyl, indolyl, quinolinyl, furanyl, benzofuranyl, thienyl, or benzothienyl, and each heteroaryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy;

wherein each heterocycloalkyl group is pyrrolidinyl, imidazolidinyl, oxazolidinyl, thiazolidinyl, tetrahydrofuranyl, piperidinyl, piperazinyl, or morpholinyl, and each heterocycloalkyl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy; and X is a leaving group.

Still more preferably, $R_{10}$ is $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl; and $R_{11}$ is H, $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl; wherein each phenyl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_4$ alkoxy, OPro, halo, $C_1$-$C_4$ haloalkyl or $C_1$-$C_4$ haloalkoxy.

In one preferred embodiment, $R_{11}$ is H.

In one preferred embodiment, $R_1$ is H and $R_2$ is H and $R_3$ is OH, methoxy or OPro, wherein the Pro group was previously defined.

In another preferred embodiment, X is halo, —$OSO_2CF_3$, —$OSO_2CH_3$, tosyl, brosyl, or nosyl.

In one embodiment, n is 0.

In another embodiment, n is 1.

In one embodiment, the methods disclosed herein are conducted in a solvent or a mixture of solvents. In general, the solvent may be an aprotic polar solvent. Non-limiting examples of suitable aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. In certain embodiments, the solvent may be tetrahydrofuran (THF), dichloromethane, dimethylformamide (DMF), dimethylacetamide (DMA), N-methylpyrrolidine (NMP) or combinations thereof. In exemplary embodiments, the methods may be conducted in DMF, DMA, NMP, or combinations thereof.

In general, the weight to weight ratio of the solvent to the compound of formula (II) may range from about 0.5:1 to about 100:1. In various embodiments, the weight ratio of the solvent to the compound of formula (II) may range from 0.5:1 to about 5:1, from about 5:1 to about 25:1, or from about 25:1 to about 100:1. In exemplary embodiments, the weight ratio of the solvent to the compound of formula (I) may range from about 0.5:1 to about 10:1.

When conducting the alkylation reaction, the solvent may further comprise a base. Examples of suitable bases include inorganic bases (such as carbonates, bicarbonates and hydroxides of the group 1 and group 2 elements of the periodic table) and amine containing bases. Examples of amine containing bases include triethylamine, diisopropylethylamine, lutidine, pyridine, or 2,6-di-tert-butyl pyridine or combinations thereof. Preferred amine bases comprise triethylamine, diisopropylethylamine and combinations thereof.

In one embodiment, $R_{25}$ is OH and $=\!=\!=$ is a single bond.

When conducting the alkylation reaction, typically from about 1 to about 10 equivalents of alkylating agent may be used. In various embodiments, the amount of alkylating agent used may range from about 1 to about 2 equivalents, from about 2 to about 4 equivalents, or from about 4 to about 10 equivalents. In one embodiment, about 1.0 to about 1.2 equivalents of alkylating agent may be used.

In an embodiment, the compound of formula (II) is noroxymorphone, and the compound of formula (I) is nalbuphine.

In another embodiment, the compound of formula (II) is noroxymorphone and the compound of formula (I) is 6α-naltrexol.

In another aspect, compounds of formula (II) are contacted with a reducing agent (as described above) and an acylating agent. Examples of acylating agents include those the formula

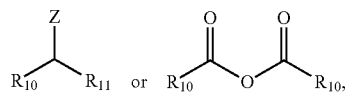

wherein Z is —C(O)-G or —SO$_2$-G, and wherein G is halo.

More preferably, $R_{10}$ is $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl; and $R_{11}$ is H, $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-aryl, —$C_2$-$C_6$ alkenyl-aryl, —$C_2$-$C_6$ alkynyl-aryl, —$C_1$-$C_6$ alkyl-heteroaryl, —$C_2$-$C_6$ alkenyl-heteroaryl, —$C_2$-$C_6$ alkynyl-heteroaryl, —$C_1$-$C_6$ alkyl-heterocycloalkyl, —$C_2$-$C_6$ alkenyl-heterocycloalkyl, —$C_2$-$C_6$ alkynyl-heterocycloalkyl, —$C_1$-$C_6$ alkyl-$C_3$-$C_8$ cycloalkyl, —$C_2$-$C_6$ alkenyl-$C_3$-$C_8$ cycloalkyl, —$C_2$-$C_6$ alkynyl-$C_3$-$C_8$ cycloalkyl, or $C_1$-$C_6$ alkoxy $C_1$-$C_6$ alkyl;

wherein each aryl group is independently phenyl or naphthyl, and each aryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy;

wherein each heteroaryl group is independently pyrrolyl, imidazolyl, triazolyl, pyridyl, pyridazinyl, pyrimidyl, pyrazinyl, triazinyl, indolyl, quinolinyl, furanyl, benzofuranyl, thienyl, or benzothienyl, and each heteroaryl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy; and wherein each heterocycloalkyl group is pyrrolidinyl, imidazolidinyl, oxazolidinyl, thiazolidinyl, tetrahydrofuranyl, piperidinyl, piperazinyl, or morpholinyl, and each heterocycloalkyl is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_6$ alkoxy, OPro, halo, $C_1$-$C_6$ haloalkyl or $C_1$-$C_6$ haloalkoxy.

Still more preferably, $R_{10}$ is $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl; and $R_{11}$ is H, $C_1$-$C_6$ alkyl, —$C_1$-$C_6$ alkyl-phenyl, $C_3$-$C_6$ cycloalkyl, —$C_1$-$C_6$ alkyl-$C_3$-$C_6$ cycloalkyl, or allyl;

wherein each phenyl group is unsubstituted or substituted at one or more substitutable positions with a group that is independently $C_1$-$C_6$ alkyl, $C_2$-$C_6$ alkenyl, $C_2$-$C_6$ alkynyl, $C_1$-$C_4$ alkoxy, OPro, halo, $C_1$-$C_4$ haloalkyl or $C_1$-$C_4$ haloalkoxy.

In one preferred embodiment, $R_{11}$ is H.

In one embodiment, G is chloro.

In another embodiment, Z is —C(O)-G and G is chloro.

In still another embodiment, Z is —SO$_2$-G, and G is chloro.

In a preferred embodiment, $R_1$ is H and $R_2$ is H and $R_3$ is OH, methoxy or OPro, wherein the Pro group was previously defined.

Still more preferably, $R_1$ is H and $R_2$ is H and $R_3$ is OH, methoxy or OPro and G is chloro.

In one embodiment, the methods disclosed herein are conducted in a solvent or a mixture of solvents. In general, the solvent may be an aprotic polar solvent. Non-limiting examples of suitable aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. In certain embodiments, the solvent may be tetrahydrofuran (THF), dichloromethane, dimethylformamide (DMF), dimethylacetamide (DMA), N-methylpyrrolidine (NMP) or combinations thereof. In exemplary embodiments, the methods may be conducted in DMF, DMA, NMP, or combinations thereof.

In general, the weight to weight ratio of the solvent to the compound of formula (II) may range from about 0.5:1 to about 100:1. In various embodiments, the weight ratio of the solvent to the compound of formula (II) may range from 0.5:1 to about 5:1, from about 5:1 to about 25:1, or from about 25:1 to about 100:1. In exemplary embodiments, the weight ratio of the solvent to the compound of formula (I) may range from about 0.5:1 to about 10:1.

When acylating the compound of formula (II), the solvent may further comprise a base. Examples of suitable bases include inorganic bases and amine containing bases. Examples of amine containing bases include triethylamine, diisopropylethylamine, lutidine, pyridine, or 2,6-di-tert-butyl pyridine or combinations thereof. Preferred amine bases comprise triethylamine, diisopropylethylamine and combinations thereof. ===

In a preferred embodiment, $R_{25}$ is OH and === is a single bond.

When conducting the acylation reaction, typically from about 1 to about 10 equivalents of acylating agent may be used. In various embodiments, the amount of acylating agent used may range from about 1 to about 2 equivalents, from about 2 to about 4 equivalents, or from about 4 to about 10 equivalents. In one embodiment, about 1.0 to about 1.2 equivalents of acylating agent may be used.

In a preferred embodiment, according to anyone of the preceding aspects and/or embodiments, $R_{14}$ is OH.

In an alternative preferred embodiment, according to anyone of the preceding aspects and/or embodiments, $R_{14}$ is H.

In a further preferred embodiments, according to anyone of the preceding aspects and/or embodiments, $R_1$ is H, $R_2$ is H and $R_3$ is OH, methoxy, or OPro.

If desired, the olefin between carbons 7 and 8 may be reduced using methods known in the art, such as Pd/C with hydrogen gas.

The reactions described above in the various aspects are typically conducted under an inert atmosphere. However, if desired, a standard atmosphere (i.e., not inert) may be used.

After the completion of the reaction(s), the resulting product may be isolated using methods known in the art, such as distillation, chromatography or the separation of diastereomeric salts.

The molar yields of the above reactions are typically better than about 80%, or 85%, or 90%.

After the completion of the above reactions, if desired, the resulting compound of formula (I) may be converted into a pharmaceutically acceptable salt. The term "pharmaceutically-acceptable salts" are salts commonly used to form alkali metal salts and to form addition salts of free acids and free bases. The nature of the salt may vary, provided that it is pharmaceutically acceptable. Suitable pharmaceutically acceptable acid addition salts of compounds of formula (I) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine), and procaine.

All of these salts may be prepared by conventional means from the corresponding compound by reacting, for example, the appropriate acid or base with the compound of formula (I).

DEFINITIONS

As used herein, "about," when referring to a numerical value, refers to that numerical value, plus or minus 10%. Thus, "about 80" should be understood to encompass the range of 72 to 88.

The terms "aryl," as used herein alone or as part of another group denote optionally substituted homocyclic aromatic groups, preferably monocyclic or bicyclic groups containing from 6 to 10 carbons in the ring portion, such as phenyl, biphenyl, naphthyl, phenanthracenyl, or anthracenyl. Preferred aryl groups include phenyl, and naphthyl, with phenyl being most preferred.

The term "heteroaryl" as used herein alone or as part of another group denotes aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furanyl, benzofuranyl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, triazinyl, indolyl, thienyl, benzothienyl, isoindolyl, indolizinyl, benzimidazolyl, indazolyl, benzotriazolyl, tetrazolopyridazinyl, carbazolyl, purinyl, quinolinyl, isoquinolinyl, and imidazopyridyl.

As used herein, "heterocycloalkyl" as used herein alone or as part of another group denotes a saturated or partially saturated three to 10 membered ring system, wherein the saturated or partially saturated ring(s) are optionally fused or bonded to other aryl groups and/or heteroaryl groups. Examples of heterocycloalkyl groups include pyrrolidinyl, imidazolidinyl, oxazolidinyl, thiazolidinyl, tetrahydrofuranyl, piperidinyl, piperazinyl, morpholinyl, thiomorpholinyl, indolinyl, and tetrahydroisoquinolinyl.

The term "hydrocarbyl" as used herein refers to organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

As used herein, "Pro" denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Greene's Protective Groups in Organic Synthesis," 4th Ed. by P. G. M. Wuts and T. W. Greene, John Wiley & Sons, Inc., 2007. Additionally, —O-Pro is equivalent to OPro.

The term "substituted hydrocarbyl" used herein refers to hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

One Pot Synthesis of Nalbuphine from Noroxymorphone

Noroxymorphone (20.00 g) and cyclobutanecarboxaldehyde (6.40 g) were stirred in DMF (40 g) for 30 min. A solution of 50% of sodium triacetoxyborohydride in DMF (32 g) was added to the above reactor over a period of 30 min, followed by addition of acetic acid (27.3 g) to form a clear solution. It was stirred at room temperature (20° C.) for 2 hr and then at 60° C. for another 1 hr after additional 50% of sodium triacetoxyborohydride in DMF (48 g) was added. Water (120 g) and then c-NH$_4$OH (60 g) were added. The suspension formed was heated at 60° C. for 1 hr, cooled down to 45° C., adjusted pH to 9.2 with c-NH$_4$OH (~20 g), and continued to cool down to rt (20° C.) for 1 hr and filtered. The wet cake collected on a filter was washed with water (60 mL) and dried at 65° C. for 18 hr to give 23.76 g of nalbuphine base as white solids. The molar yield was 95.5% (equal to 118.8% wt/wt yield) and 6-α-OH:6-β-OH ratio was 98.9:0.10.

Example 2

One Pot Synthesis of 6-α-Naltrexol from Noroxymorphone

Noroxymorphone (20.00 g) and cyclopropanecarboxaldehyde (5.40 g) were stirred in DMF (40 g) for 60 min. A solution of 50% of sodium triacetoxyborohydride in DMF (35 g) was added to the above reactor over a period of 2 hr, followed by addition of acetic acid (27.3 g) to form a clear solution. It was stirred at room temperature (20° C.) for 2 hr and then at 60° C. for another 1 hr after additional 50% of sodium triacetoxyborohydride in DMF (45 g) was added. Water (120 g) and then c-NH$_4$OH (60 g) were added. The suspension formed was heated at 60° C. for 1 hr, cooled down to 45° C., adjusted pH to 9.2 with c-NH$_4$OH (~20 g), and continued to cool down to rt (20° C.) for 1 hr and filtered. The wet cake collected on a filter was washed with water (60 mL) and dried at 65° C. for 18 hr to give 18.71 g of 6-α-naltrexol base as white solids. The molar yield was 78% (equal to 93.6% wt/wt yield) and 6-α-OH:6-β-OH ratio was 98.74:0.07.

Example 3

Conversion of Noroxymorphone to Nalbuphone

Noroxymorphone (20.00 g) and cyclobutanecarboxaldehyde (1.60 g) were stirred in DMF (10 g) for 30 min. A solution of 40% of sodium triacetoxyborohydride in DMF (11.5 g) was added to the above reactor over a period of 15 min. HPLC analysis indicated that there was 97.0% of product formed in the solution.

Example 4

Conversion of Noroxymorphone to Naltrexone

Noroxymorphone (20.00 g) and cyclopropanecarboxaldehyde (5.40 g) were stirred in DMF (40 g) for 60 min. A solution of 50% of sodium triacetoxyborohydride in DMF (35 g) was added to the above reactor over a period of 2 hr. HPLC analysis indicated that there was 90% of product formed in the solution.

What is claimed is:

1. A method for preparing a compound of formula (I)

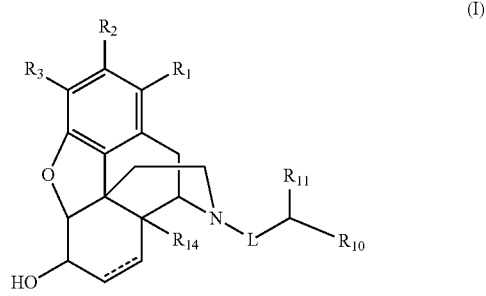

(I)

the method comprising,
(a) contacting a compound of formula (II)

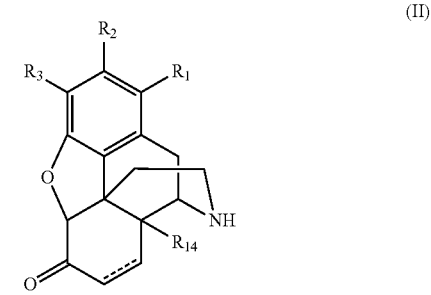

(II)

with a carbonyl compound having formula:

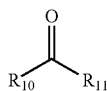

to form an intermediate compound; and
(b) contacting the intermediate compound with a boron based reducing agent at a temperature of 0° C. or greater to form the compound of formula (I);
wherein:
=== is a single or double bond;
$R_1$ is H, $C_1$-$C_6$ alkyl, $C_1$-$C_6$ alkoxy, OH, or —O-Pro;
$R_2$ is H, $C_1$-$C_6$ alkyl, $C_1$-$C_6$ alkoxy, OH, or —O-Pro;
$R_3$ is H, $C_1$-$C_6$ alkyl, $C_1$-$C_6$ alkoxy, OH, or —O-Pro, wherein
Pro, at each occurrence, is independently a hydroxyl protecting group;
$R_{10}$ is $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-$C_3$-$C_8$ cycloalkyl, -$C_2$-$C_6$ alkenyl-$C_3$-$C_8$ cycloalkyl, -$C_2$-$C_6$ alkynyl-$C_3$-$C_8$ cycloalkyl, or $C_1$-$C_6$ alkoxy-$C_1$-$C_6$ alkyl;
$R_{11}$ is H, $C_1$-$C_6$ alkyl, $C_2$-$C_6$ alkenyl, $C_2$-$C_6$ alkynyl, $C_3$-$C_8$ cycloalkyl, —$C_1$-$C_6$ alkyl-$C_3$-$C_8$ cycloalkyl, -$C_2$-$C_6$ alkenyl-$C_3$-$C_8$ cycloalkyl, -$C_2$-$C_6$ alkynyl-$C_3$-$C_8$ cycloalkyl, or $C_1$-$C_6$ alkoxy-$C_1$-$C_6$ alkyl; and
$R_{14}$ is H or OH.

2. The method of claim 1, wherein $R_1$ is H; $R_2$ is H; and $R_3$ is OH, methoxy or OPro.

3. The method of claim 1, wherein the compound of formula (I) comprises a mixture of 6-α-hydroxy and 6-β-hydroxy epimers, the mixture of epimers having an epimeric ratio of 6-α-hydroxy to 6-α-hydroxy epimers of greater than or equal to 9:1.

4. The method of claim 1, wherein the boron reducing agent comprises $MBH_nR_{4-n}$, wherein M is Li, Na, or K; n is 1 or 2; and each R is independently —$O_2C$—($C_1$-$C_5$ alkyl).

5. The method of claim 1, wherein
$R_{10}$ is $C_1$-$C_6$ alkyl, $C_3$-$C_6$ cycloalkyl, —$C_1$-$C_6$ alkyl-$C_3$-$C_6$ cycloalkyl, or allyl; and
$R_{11}$ is H, $C_1$-$C_6$ alkyl, $C_3$-$C_6$ cycloalkyl, —$C_1$-$C_6$ alkyl-$C_3$-$C_6$ cycloalkyl, or allyl.

6. The method of claim 5, wherein the boron reducing agent comprises $MBH_nR_{4-n}$, wherein M is Li, Na, or K; n is 1 or 2; and each R is independently —$O_2C$—($C_1$-$C_5$ alkyl).

7. The method of claim 6, the contacting is conducted in a solvent chosen from DMF, DMA, NMP, or combinations thereof.

8. The method of claim 7, wherein the solvent further comprises an acid.

9. The method of claim 1, wherein the compound of formula (II) is noroxymorphone and the compound of formula (I) is nalbuphine or 6-α-naltrexol.

10. A method for preparing a compound of Formula (Ia) from a compound of formula (IIa), the method comprising:
(a) contacting the compound of formula (IIa) with a carbonyl compound having formula

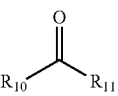

to form an intermediate compound; and
(b) contacting the intermediate compound with a boron based reducing agent at a temperature of 0° C. or greater to form the compound of formula (Ia), according to the following reaction scheme:

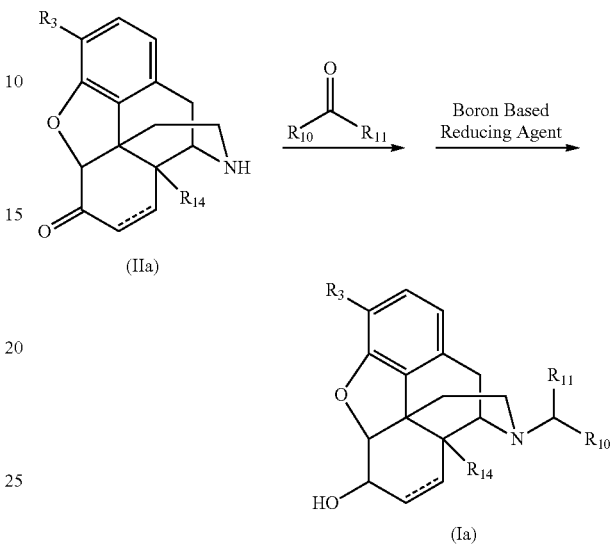

wherein:
=== is a single or double bond;
$R_3$ is $C_1$-$C_6$ alkoxy, OH, or O-Pro; wherein Pro is a hydroxyl protecting group;
$R_{10}$ is $C_1$-$C_6$ alkyl, $C_2$-$C_6$ alkenyl, $C_2$-$C_6$ alkynyl, $C_3$-$C_8$ cycloalkyl, or C-$_1$-$C_6$ alkyl-$C_3$-$C_8$ cycloalkyl;
$R_{11}$ is H, $C_1$-$C_6$ alkyl, $C_2$-$C_6$ alkenyl, $C_2$-$C_6$ alkynyl, $C_3$-$C_8$ cycloalkyl, or $C_1$-$C_6$ alkyl-$C_3$-$C_8$ cycloalkyl; and
$R_{14}$ is H or OH.

11. The method of claim 10, wherein the boron reducing agent comprises $MBH_nR_{4-n}$, wherein M is Li, Na, or K; n is 1 or 2; and each R is independently —$O_2C$—($C_1$-$C_5$ alkyl).

12. The method of claim 10, wherein $R_3$ is OH or methoxy.

13. The method of claim 12, wherein $R_{10}$ is $C_3$-$C_6$ cycloalkyl and $R_{11}$ is H.

14. The method of claim 13, wherein the boron based reducing agent is a triacetoxyborohydride.

15. The method of claim 14, wherein the contacting is conducted in a solvent chosen from DMF, DMA, NMP, or combinations thereof.

16. The method of claim 15, wherein the solvent further comprises an acid.

17. The method of claim 10, wherein the compound of formula (Ia) comprises a mixture of 6-α-hydroxy and 6-β-hydroxy epimers, the mixture of epimers having an epimeric ratio of 6-α-hydroxy to 6-βhydroxy epimers of greater than or equal to 9:1.

18. The method of claim 10, wherein the compound of formula (IIa) and the compound of formula (Ia) independently have an optical activity of (−) or (+), and carbons C-5, C-13, C-14, and C-9, respectively, have a configuration of RRRR, RRSR, RRRS, RRSS, RSRR, RSSR, RSRS, RSSS, SRRR, SRSR, SRRS, SRSS, SSRR, SSSR, SSRS, or SSSS, provided that carbons C-15 and C-16 are both either on the alpha face of the molecule or the beta face of the molecule.

* * * * *

UNITED STATES PATENT AND TRADEMARK OFFICE
CERTIFICATE OF CORRECTION

PATENT NO. : 9,499,556 B2
APPLICATION NO. : 14/529368
DATED : November 22, 2016
INVENTOR(S) : Peter X. Wang et al.

It is certified that error appears in the above-identified patent and that said Letters Patent is hereby corrected as shown below:

In the Claims

Column 15, Line 29, "OH." should be --OH, and L is absent.--

Signed and Sealed this
Sixteenth Day of May, 2017

Michelle K. Lee
*Director of the United States Patent and Trademark Office*